US007923448B2

(12) United States Patent
Nedergaard et al.

(10) Patent No.: US 7,923,448 B2
(45) Date of Patent: Apr. 12, 2011

(54) PURINE RECEPTOR INHIBITION AS A THERAPEUTIC STRATEGY IN SPINAL CORD AND BRAIN

(75) Inventors: Maiken Nedergaard, Webster, NY (US); Steven A. Goldman, Webster, NY (US)

(73) Assignees: Cornell Research Foundation, Inc., Ithaca, NY (US); New York Medical College, Valhalla, NY (US)

( * ) Notice: Subject to any disclaimer, the term of this patent is extended or adjusted under 35 U.S.C. 154(b) by 1238 days.

(21) Appl. No.: 10/979,526

(22) Filed: Nov. 2, 2004

(65) Prior Publication Data

US 2005/0164975 A1 Jul. 28, 2005

Related U.S. Application Data

(60) Provisional application No. 60/516,677, filed on Nov. 3, 2003.

(51) Int. Cl.
*A61K 31/497* (2006.01)
*A61K 31/4965* (2006.01)
*A61K 31/70* (2006.01)
*A01N 43/04* (2006.01)

(52) U.S. Cl. ... 514/253.05; 514/47; 514/50; 514/255.06

(58) Field of Classification Search ............ 514/47, 514/50, 253.05, 255.06
See application file for complete search history.

(56) References Cited

U.S. PATENT DOCUMENTS

| | | | |
|---|---|---|---|
| 6,133,434 A | 10/2000 | Buell et al. | |
| 6,469,055 B2 | 10/2002 | Lee et al. | |
| 6,608,085 B1 | 8/2003 | Gillespie et al. | |
| 6,787,541 B1 | 9/2004 | Gillespie et al. | |
| 2003/0129134 A1 | 7/2003 | Chenard et al. | |

OTHER PUBLICATIONS

Ferrari et al. FEBS Letters, 1999. vol. 447, pp. 71-75.*
Hausmann, O N. Spinal Cord, Jul. 2003, vol. 41, pp. 369-378).*
Arcuino et al., "Intercellular Calcium Signaling Mediated by Point-Source Burst Release of ATP," *Proc. Natl. Acad. Sci. USA* 99:9840-9845 (2002).
Barnard et al., "Nucleotide Receptors in the Nervous System," *Molecular Neurobiology* 15(2):103-129 (1997).
Basso et al., "A Sensitive and Reliable Locomotor Rating Scale for Open Field Testing in Rats," *J. Neurotrauma* 12(1):1-21 (1995).
Chow et al., "Purines and Their Roles in Apoptosis," *Neuropharmacology* 36(9):1149-1156 (1997).
Cook et al., "Cell Damage Excites Nociceptors Through Release of Cytosolic ATP," *Pain* 95(1-2):41-47 (2002).
Cotrina et al., "Connexins Regulate Calcium Signaling by Controlling ATP Release," *Proc. Natl. Acad. Sci. USA* 95:15735-15740 (1998).
Deuchars et al., "Neuronal $P2X_7$ Receptors Are Targeted to Presynaptic Terminals in the Central and Peripheral Nervous Systems," *J. Neurosci.* 21(18):7143-7152 (2001).
Di Virgilio et al., "Cytolytic P2X Purinoceptors," *Cell Death Differ.* 5(3):191-199 (1998).
Du et al., "Calcium Influx and Activation of Calpain I Mediate Acute Reactive Gliosis in Injured Spinal Cord," *Exp. Neurol.* 157(1):96-105 (1999).
Fields et al., New Insights Into Neuron-Glia Communication, *Science* 298(5593):556-562 (2002).
Guthrie et al., "ATP Released From Astrocytes Mediates Glial Calcium Waves," *J. Neurosci.* 19(2):520-528 (1999).
Haydon, "GLIA: Listening and Talking to the Synapse," *Nat. Rev. Neurosci.* 2(3):185-193 (2001).
Karmazyn, M., "$Na^+/H^+$ Exchange Inhibitors Reverse Lactate-Induced Depression in Postischaemic Ventricular Recovery," *Br. J. Pharmacol.* 108:50-56 (1993).
Khakh et al., "Neuronal P2X Transmitter-Gated Cation Channels Change Their Ion Selectivity in Seconds," *Nat. Neurosci.* 2(4):322-330 (1999).
Lin et al., "Connexin Mediates Gap Junction-Independent Resistance to Cellular Injury," *J. Neurosci.* 23(2):430-441 (2003).
Lin et al., "Gap-Junction-Mediated Propagation and Amplification of Cell Injury," *Nat. Neurosci.* 1(6):494-500 (1998).
Neary et al., "Activation of Extracellular Signal-Regulated Kinase by Stretch-Induced Injury in Astrocytes Involves Extracellular ATP and P2 Purinergic Receptors," *J. Neurosci.* 23(6):2348-2356 (2003).
Nedergaard et al., "Characterization of Cortical Depolarization Evoked in Focal Cerebral Ischemia," *J. Cereb. Blood Flow Metab.* 13(4):568-574 (1993).
Nilsson et al., "Regional Changes in Interstitial K+ and $Ca^{2+}$ Levels Following Cortical Compression Contusion Trauma in Rats," *J. Cereb. Blood Flow Metab.* 13(2):183-192 (1993).
North, "Molecular Physiology of P2X Receptors," *Physiol. Rev.* 82(4):1013-1067 (2002).
Stokes et al., "Extracellular Calcium Activity in the Injured Spinal Cord," *Exp. Neurol.* 80(3):561-572 (1983).
Stout et al., "Modulation of Intercellular Calcium Signaling in Astrocytes by Extracellular Calcium and Magnesium," *Glia* 43(3):265-273 (2003).
Takano et al., "Glutamate release Promotes Growth of Malignant Glioma," *Nat. Med.* 7(9):1010-1015 (2001).

* cited by examiner

*Primary Examiner* — Sreeni Padmanabhan
*Assistant Examiner* — Samira Jean-Louis
(74) *Attorney, Agent, or Firm* — LeClairRyan

(57) ABSTRACT

The present invention is directed to a method of treating a subject with acute spinal cord injury by administering a purine receptor antagonist to the subject under conditions effective to treat spinal cord injury. The purine receptor antagonist inhibits P2X purine receptor activation. The inhibition of P2X purine receptor activation can also be used in conjunction with methods of treating a subject with spinal cord ischemia resulting from stroke or vascular insult, interruption, or mechanical injury, treating a subject with ischemic or traumatic insults of brain tissue in regions expressing P2X receptors, and for inhibiting ATP-triggered brain or spinal cord cell death.

26 Claims, 5 Drawing Sheets

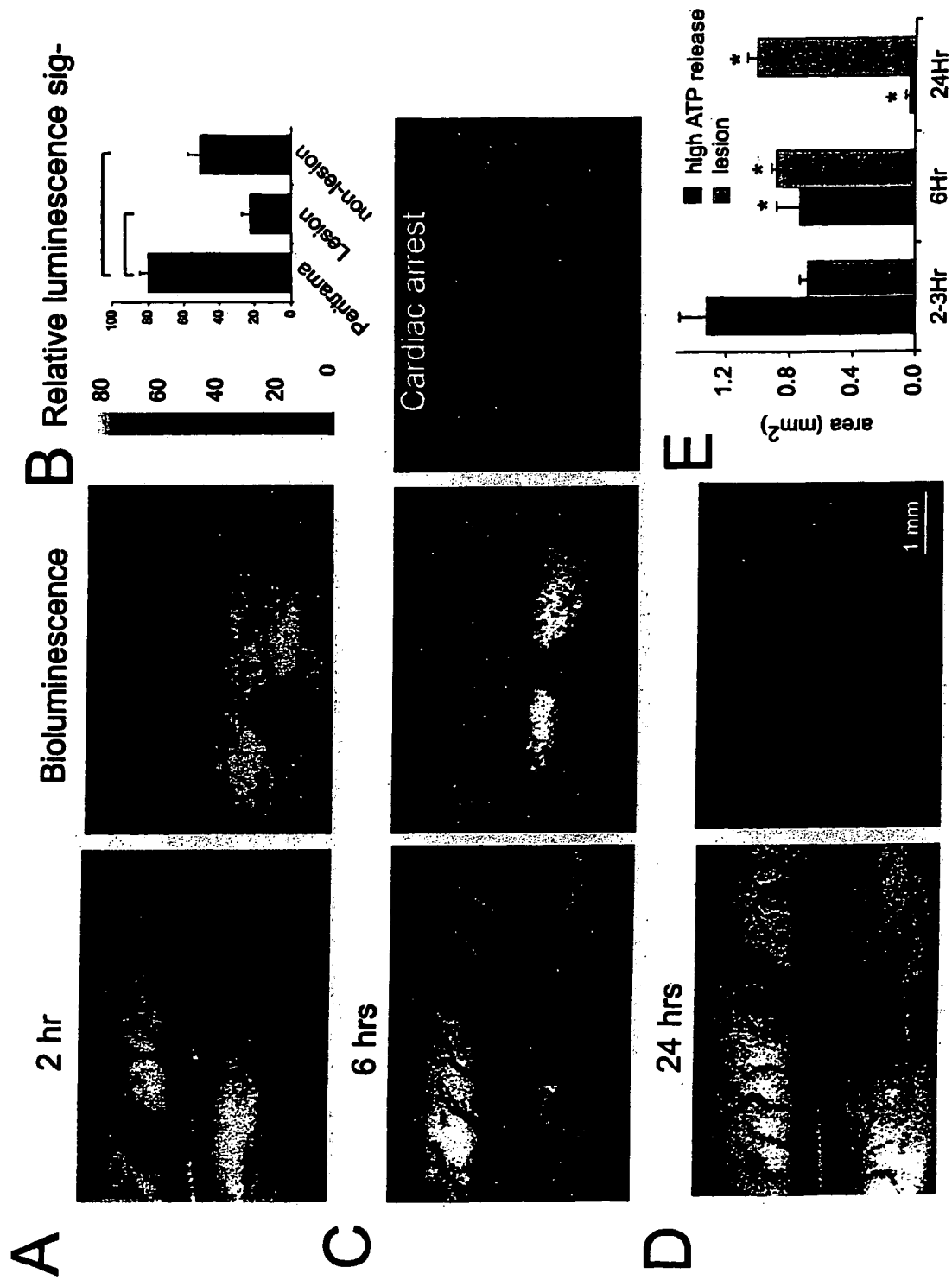
Figures 1A-E

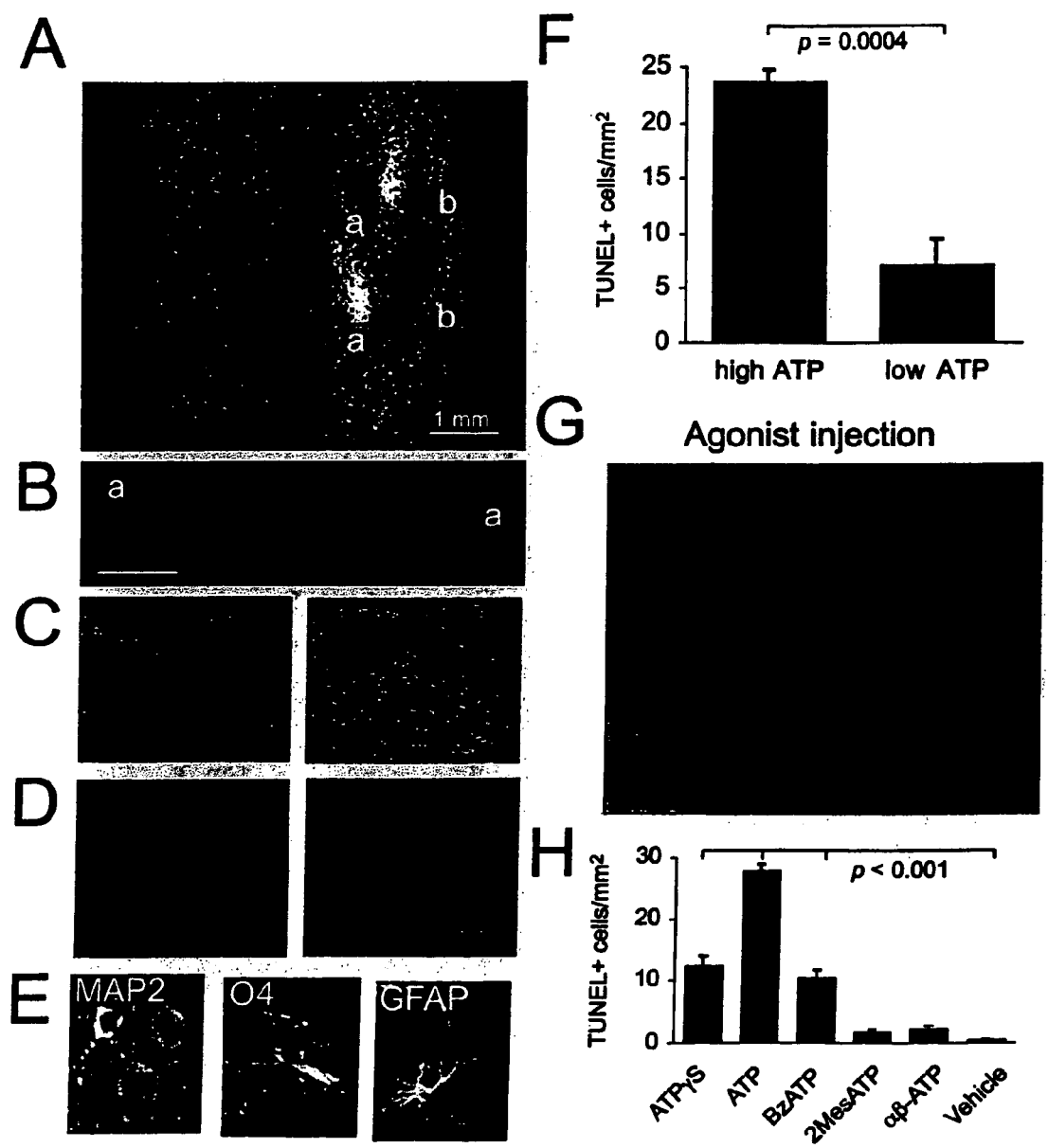
Figures 2A-H

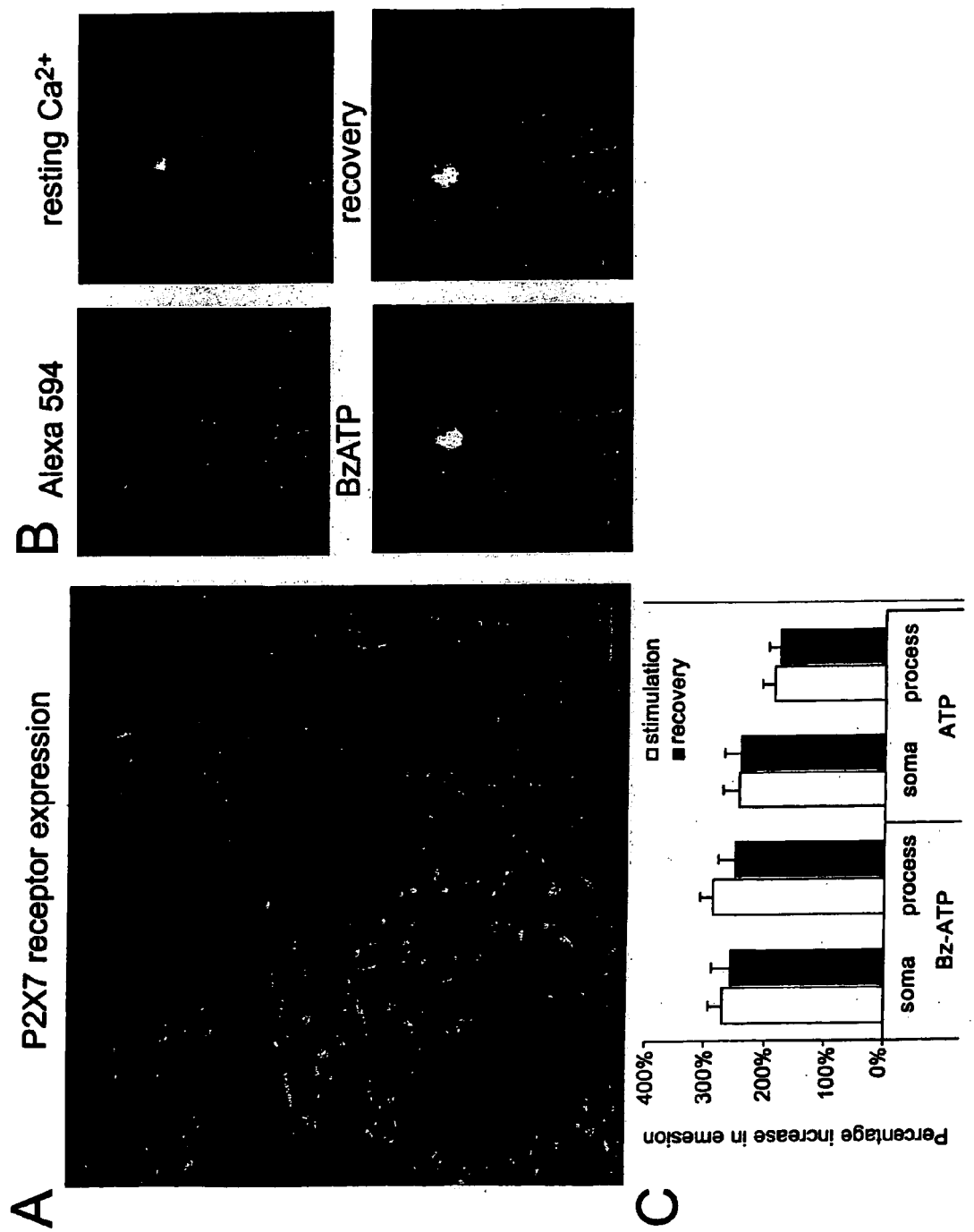
Figures 3A-C

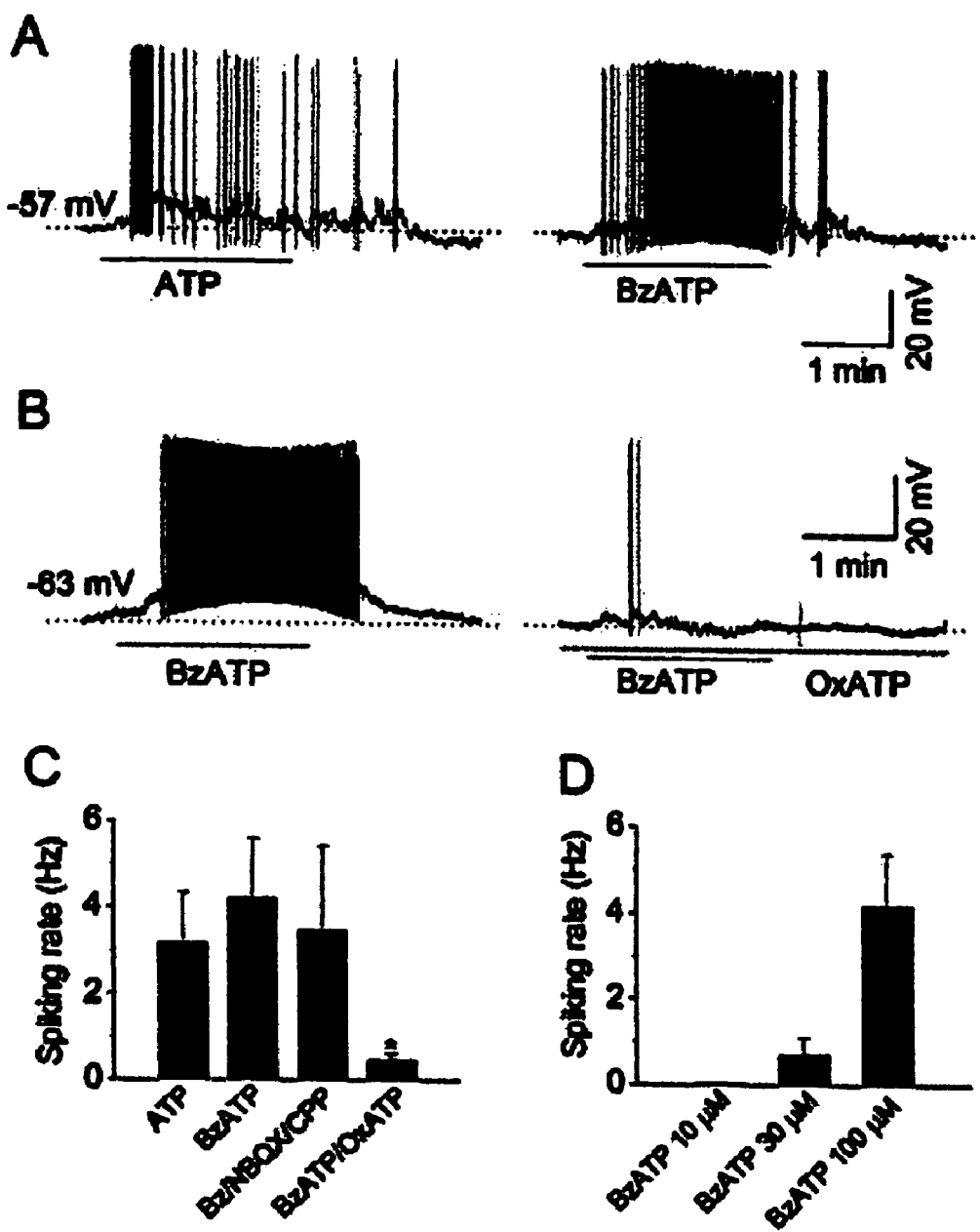
Figures 4A-D

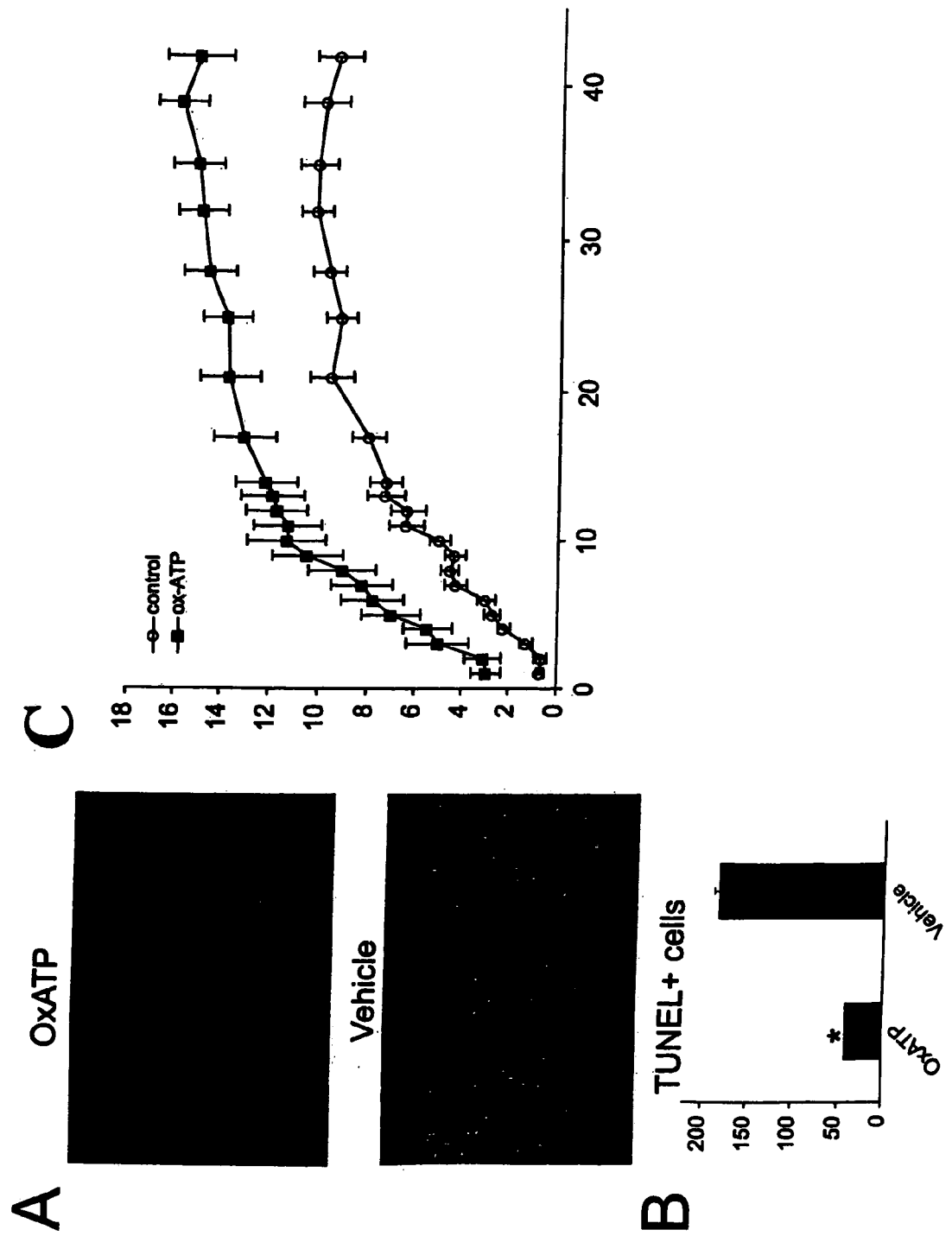
Figures 5A-C

PURINE RECEPTOR INHIBITION AS A THERAPEUTIC STRATEGY IN SPINAL CORD AND BRAIN

This application claims the benefit of U.S. Provisional Patent Application Ser. No. 60/516,677, filed Nov. 3, 2003.

This invention was made with government support under grant 30007 awarded by National Institute of Neurological Disorders and Stroke. The government has certain rights in the invention.

FIELD OF THE INVENTION

The present invention is directed to inhibition of purine receptors as a therapeutic strategy in spinal cord and brain injury.

BACKGROUND OF THE INVENTION

Acute spinal injury is a major public health problem. Spinal cord injuries resulting in paralysis or other severe neurological morbidity are caused by both acute trauma and acute manifestations of systemic disease. Traumatic spinal cord injury is biased toward young people and can lead to life-long paraparesis or quadriparesis. Acute spinal cord trauma is caused by motor vehicle accidents, falls, diving accidents, penetrating wounds (e.g., gunshots and knife wounds), and sports-related incidents. Acute spinal injuries reflecting systemic disease include acute epidural compression of the spinal cord. Causes of acute epidural spinal cord compression include ruptured discs, metastatic tumor, infection with acute epidural abcess, acute ischemic manifestation of osteophytes, vertebral collapse due to tumors, osteopenia, osteoporosis, or rheumatoid arthritis. There is currently no effective treatment for spinal cord pathology in any of these conditions, with the exception of high-dose glucocorticoid treatment of acute traumatic spinal cord injury which, although clinically accepted, has minimal efficacy.

In addition to the primary injury to the spinal cord, in the days after initial injury, secondary injury occurs. This occurs as the effects of the initial injury spread. Secondary injury complicates functional recovery following spinal cord injury, but the mechanisms leading to degeneration of tissue outside traumatic lesions has been poorly understood.

The present invention is directed to overcoming the deficiencies in the art.

SUMMARY OF THE INVENTION

The present invention is directed to a method of treating a subject with acute spinal cord injury. This method involves administering a purine receptor antagonist to the subject under conditions effective to treat spinal cord injury. The purine receptor antagonist inhibits P2X purine receptor activation.

Another aspect of the present invention is directed to a method of treating a subject with spinal cord ischemia resulting from stroke or vascular insult, interruption, or mechanical injury. This method involves administering a purine receptor antagonist to the subject under conditions effective to treat spinal cord spinal cord ischemia resulting from stroke or vascular insult, interruption, or mechanical injury. The purine receptor antagonist inhibits P2X purine receptor activation.

A further aspect of the present invention relates to a method of treating a subject with ischemic or traumatic insults of brain tissue in regions expressing P2X receptors. This method involves administering a purine receptor antagonist to the subject under conditions effective to treat ischemic or traumatic insults of brain tissue in regions expressing P2X receptors. The purine receptor antagonist inhibits P2X purine receptor activation.

Another aspect of the present invention relates to a method of inhibiting ATP-triggered brain or spinal cord cell death. This method is carried out by contacting brain or spinal cord cells with a purine receptor antagonist under conditions effective to inhibit ATP-triggered brain or spinal cord cell death. The purine receptor antagonist inhibits P2X purine receptor activation.

In addition to mediating neurotransmission, ATP has recently been identified as a potent transmitter of astrocytic calcium signaling (Cotrina et al., "Connexins Regulate Calcium Signaling by Controlling ATP Release," *Proc Natl Acad Sci USA* 95:15735-15740 (1998); and Guthrie et al., "ATP Released From Astrocytes Mediates Glial Calcium Waves," *J Neurosci* 19:520-528 (1999), which are hereby incorporated by reference in their entirety). Astrocytes release ATP through a regulated pathway, resulting in propagating intercellular waves of cytosolic calcium entry (Arcuino et al., "Intercellular Calcium Signaling Mediated by Point-Source Burst Release of ATP," *Proc Natl Acad Sci USA* 99:9840-9845 (2002), which is hereby incorporated by reference in its entirety). Astrocytic calcium signaling appears to be a general mechanism by which astrocytes respond to variety of stimuli, including synaptic activity, transmitter exposure, and traumatic injury (Fields et al., New insights Into Neuron-Glia Communication," *Science* 298:556-562 (2002), which is hereby incorporated by reference in its entirety). In turn, astrocytic calcium signals are transmitted to adjacent neurons, whose synaptic strength may thereby be modulated (Haydon, "GLIA: Listening and Talking to the Synapse," *Nat Rev Neurosci* 2:185-193 (2001), which is hereby incorporated by reference in its entirety). By this means, local astrocytes may transmit distant calcium signals to neurons within their own geographic microdomain, thereby transducing regional signals to local changes in synaptic efficacy. This ATP-dependent process of calcium wave propagation may occur not only in the brain, within which it has been best studied in situ, but also in the parenchyma of the spinal cord.

Since calcium wave propagation has been noted to expand the effective radius of parenchymal brain and spinal cord injury, and since calcium wave propagation is mediated through ATP release, applicants questioned if spinal cord injury in particular is associated with excessive ATP release, and whether ATP per se is deleterious to threatened spinal cord neurons. Applicants specifically asked whether excessive ATP release might lead to spinal neuronal death via activation of neuronal P2X receptors. This idea is based on the observations that: 1) ATP release and astrocytic $Ca^{2+}$ signaling are both triggered by traumatic injury (Cook et al., "Cell Damage Excites Nociceptors Through Release of Cytosolic ATP," *Pain* 95:41-47 (2002); Neary et al., "Activation of Extracellular Signal-Regulated Kinase by Stretch-Induced Injury in Astrocytes Involves Extracellular ATP and P2 Purinergic Receptors," *J Neurosci* 23:2348-2356 (2003); and Du et al., "Calcium Influx and Activation of Calpain I Mediate Acute Reactive Gliosis in Injured Spinal Cord," *Exp Neurol* 157:96-105 (1999), which are hereby incorporated by reference in their entirety); 2) traumatic injury is associated with a decrease in extracellular $Ca^{2+}$, that enhances both astrocytic ATP release and $Ca^{2+}$ signaling (Stokes et al., "Extracellular Calcium Activity in the Injured Spinal Cord," *Exp Neurol* 80:561-572 (1983); Nilsson et al., "Regional Changes in Interstitial K+ and Ca2+ Levels Following Cortical Compression Contusion Trauma in Rats," *J Cereb Blood Flow Metab*

13:183-192 (1993); Stout et al., "Modulation of Intercellular Calcium Signaling in Astrocytes by Extracellular Calcium and Magnesium," *Glia* 43:265-273 (2003); Cotrina et al., "Connexins Regulate Calcium Signaling by Controlling ATP Release," *Proc Natl Acad Sci USA* 95:15735-15740 (1998), which are hereby incorporated by reference in their entirety); P2X7 receptor activation by excessive ATP may directly mediate cell death (Di Virgilio et al., "Cytolytic P2X Purinoceptors," *Cell Death Differ* 5:191-199 (1998), which is hereby incorporated by reference in its entirety); and 4) spinal cord neurons, including motor neurons, express P2X7 receptors (Deuchars et al., "Neuronal P2X7 Receptors Are Targeted to Presynaptic Terminals in the Central and Peripheral Nervous Systems," *J Neurosci* 21:7143-7152 (2001), which is hereby incorporated by reference in its entirety).

BRIEF DESCRIPTION OF THE DRAWINGS

FIGS. 1A-E show that bioluminescence detection of ATP release following acute spinal cord injury. FIG. 1A is a brightfield image of the exposed spinal cord (T12) 2 hrs after a weight drop impact (left panel). Bioluminescence image of ATP release from the same animals (middle panel). The traumatic lesion display low ATP release but is surrounded by a peri-traumatic zone with high ATP release. FIG. 1B shows a comparison of relative luminescence signal from the traumatic lesion, peri-traumatic zone with high ATP release, and opposite side 2 hrs after impact (n=10). FIG. 1C shows a bright field image of post traumatic spinal cord 6 hrs after impact (left panel). Persistent high ATP release is evident in peri-traumatic zone (middle panel). Ten minutes after cardiac arrest, ATP release in the peri-traumatic zone has ceased to background level (right panel). FIG. 1D shows a bright field image 24 hrs after impact (left panel). Bioluminescence imaging of ATP release 24 hrs after injury did not reveal areas of high ATP (n=6). FIG. 1E shows a comparison of the area of the lesion and the peri-traumatic zone with high ATP release at 2-3, 6, and 24 hrs. $p<0.05$, ANOVA, Tukey/Kramer posthoc test.

FIGS. 2A-H show the apoptosis in areas of high ATP release. FIG. 2A is a bioluminescence image of ATP release 2 hrs after weight drop impact. DiIC18 was injected 200 µm into the spinal cord at position a. b-b indicate a mirror opposite site in equal distance to the lesion site. FIG. 2B shows the fluorescence detection of $DiI_{C18}$ injection sites. FIG. 2C shows how luxol fast blue revealed loss of myelin in between areas a-a, but less so between b-b. FIG. 2D shows how TUNEL staining revealed apoptotic cells but less so between b-b. FIG. 2E shows how TUNEL staining (red) of MAP2 positive neurons (white, left panel), O4 positive oligodendrocytes (white, middle panel), but not of GFAP positive astrocytes (white, right panel). FIG. 2F is a comparison of the number of TUNEL-positive cells in animals undergoing bioluminescence imaging, dye injection, and postive identification of area a-a and b-b. $p<0.001$ (student t-test). FIG. 2G shows how injection of ATP or agonists induces apoptosis in the non-injured spinal cord. TUNEL-positive cells 24 hrs following injection of ATP. FIG. 2H is a comparison of number of apoptotic cells following injection of ATPγS, ATP, BzATP, 2MesATP, αβATP, and vehicle.

FIGS. 3A-C show expression of functional P2X7 receptors by motor neurons revealed by 2-photon laser scanning microscopy. FIG. 3A shows the immunofluorescence detection of P2X7 receptors (red) localized in the membrane of MAP-2 positive (white) spinal cord neurons. Counterstained with a nuclear marker Sytox (green). FIG. 3B shows how BzATP induces an irreversible increase in neuronal cytosolic calcium in acutely prepared spinal cord slices. The neuron was patched in current-clamp at its resting membrane potential (baseline, −57 mV) with a pipette containing fluo-4 (100 µM) and Alexa Fluor-594 (50 µM). Bath application of 100 µM BzATP induced a calcium elevation detected by an increase in fluo-4 emission in the cell body as well as the processes. The calcium elevation failed to recover after washout (20 min exposure to BzATP followed by 20 min washout). FIG. 3C shows a summary of calcium imaging experiments. Histogram map peak increases in fluo-4 signal during Bz-ATP (100 µM, left) and ATP (100 µM, right) and after 15-20 min washout.

FIGS. 4A-D show P2X7 receptor activation induces high frequency firing in spinal cord neurons. Action potential triggered by bath application of 100 µM ATP (FIG. 4A, right panel) or 100 µM BzATP (FIG. 4A, left panel) firing in the same neuron. OxATP (100 µM), an antagonist of P2X7 receptor, prevented BzATP-induced action potential firing (FIG. 4B). The interval between the applications is 6 min. Average spiking rate under various experimental conditions. Both ATP (100 µM, n=6) and BzATP (100 µM, n=9) increase spiking rate (FIG. 4C). Combined application of NBQX (10 µM, AMPA antagonist) and CPP (5 µM, NMDA antagonist) had no significant effect on BzATP-induced increase in spiking firing rate ($p>0.05$, n=6). OxATP (100 µM) prevented BzATP-induced increase in spike rate (*, $p<0.01$, n=7). FIG. 4D shows the spiking rate increases in a dose-dependent manner after addition of BzATP (n=5-9).

FIGS. 5A-C show how a P2X7 receptor antagonist reduces apoptosis, size of the traumatic lesion and improves functional recovery following spinal cord injury. FIG. 5A shows tunel-positive cells 24 hrs after spinal cord injury in animals treated with OxATP versus vehicle. FIG. 5B shows a comparison of number of TUNEL-positive cells in animals treated with OxATP or vehicle 24 hrs after injury. $P<0.001$ (student t-test). FIG. 5C shows functional recovery evaluated by the BBB scale for 6 weeks following spinal cord injury. N=14 in both groups. *, $P<0.01$, ** $P<0.001$, OxATP treated group compared with control group. Data represent mean±s.e.m.

DETAILED DESCRIPTION OF THE INVENTION

The present invention is directed to a method of treating a subject with acute spinal cord injury. This method involves administering a purine receptor antagonist to the subject under conditions effective to treat spinal cord injury. The purine receptor antagonist inhibits P2X purine receptor activation.

Although a variety of subjects can be treated in accordance with this method, it is particularly preferred that the subject be a human.

The surface receptors for extracellular nucleotides are called P2 receptors. Previously, they were called P2 purinoreceptors, but it is now realized that some P2 receptors are activated by both pyrimidine and purine nucleotides. Thus, the nomenclature has changed to reflect the varied nature of ligands for P2 receptors. The current nomenclature system for P2 receptors is based on molecular structure and signal transduction mechanisms to define families of ionotropic P2X receptors (ligand-gated ion channels) and metabotropic P2Y receptors (G protein-coupled receptors).

P2X receptors are ATP-gated cation channels that mediate fast excitatory transmission in diverse regions of the brain and in spinal cord (North, "Molecular Physiology of P2X Receptors," *Physiol Rev* 82:1013-1067 (2002), which is hereby incorporated by reference in its entirety). Several P2X receptor subtypes have the unusual property of changing their ion selectivity during prolonged exposure to ATP. Brief exposure to ATP induces opening of channels permeable to $Na^+$ and $K^+$, whereas longer exposures of seconds to minutes duration result in progressive dilatation of the channel pore, and permeability to larger cations, as well as to fluorescent indicators such as propidium, YO-PRO-1, and ethidium (Khakh et al., "Neuronal P2X Transmitter-Gated Cation Channels Change Their Ion Selectivity in Seconds," *Nat Neurosci* 2:322-330 (1999), which is hereby incorporated by reference in its entirety). The P2X7 receptor was originally described in cells of hematopoietic origin, among which its activation has been linked to cell lysis, an apparent consequence of efflux of essential metabolites and intracellular messengers (Di Virgilio et al., "Cytolytic P2X Purinoceptors," *Cell Death Differ* 5:191-199 (1998), which is hereby incorporated by reference in its entirety). Yet although the P2X7 receptor has been reported in the nervous system, its functional role in both the brain and spinal cord have remained unexplored.

Members of the existing family of ionotropic P2X1-7 receptors show a subunit topology of i) intracellular N- and C-termini possessing consensus binding motifs for protein kinases, ii) two transmembrane spanning regions (TM1 and TM2), the first involved with channel gating and second lining the ion pore, iii) large extracellular loop, with 10 conserved cysteine residues forming a series of disulphide bridges, iv) hydrophobic H5 region close to the pore vestibule, for possible receptor/channel modulation by cations (magnesium, calcium, zinc, copper and protons ions), and v) an ATP-binding site, which may involve regions of the extracellular loop adjacent to TM1 and TM2. The P2X1-7 receptors show 30-50% sequence identity at the peptide level. The stoichiometry of P2X1-7 receptors is now thought to involve three subunits which form a stretched trimer. See Barnard et al., "Nucleotide Receptors in the Nervous System," *Molecular Neurobiology* pp. 103-129 (1997), which is hereby incorporated by reference in its entirety.

P2X1-5,7 receptors can form homomultimeric assemblies by using the same subunits, although in some tissues, P2X receptors exist as heteromultimeric assemblies (P2X2/3 in nodose ganglia, P2X2/6 and P2X4/6 in CNS neurons, P2X1/5 in some blood vessels). The P2X receptor family shows many pharmacological operational differences. Agonist potency orders can vary significantly between P2X subtypes, and some (P2X4 and P2X4/6) are relatively insensitive to known P2 receptor antagonists. The kinetics of activation, inactivation, and deactivation also vary considerably amongst P2X receptors. Calcium permeability is high for some P2X subtypes, a property that may be functionally important. The P2X7 subtype converts to a pore and, in some cases, brings about cell death. Several other P2X receptors (P2X2, P2X2/3, P2X4 and P2X2/6) also show time-dependent changes in their ion permeability properties of their intrinsic ion channel. See Barnard et al., "Nucleotide Receptors in the Nervous System," *Molecular Neurobiology* pp. 103-129 (1997), which is hereby incorporated by reference in its entirety.

In carrying out the present invention, particularly suitable P2X7 purine receptor antagonists include 1-[N,O-bis(5-Isoquinolinesulfonyl)-N-methyl-L-tyrosyl]-4-phenylpiperazine, hexamethylene amiloride, oxidized ATP, and brilliant blue G.

Although P2X7 are particularly useful in carrying out the present invention, P2X1, P2X2, P2X3, P2X4, P2X5, and P2X6 purine receptor antagonists can also be utilized.

Suitable P2X1 receptor antagonists include pyridoxal-5'-phosphate-6-azophenyl-2',5'-disulphonic acid, diinosine pentaphosphate, pyridoxal-5'-phosphate-6-azophenyl-4'-carboxylate, 8,8'-(carbonylbis(imino-3,1-phenylenecarbonylimino)bis(1,3,5-napththalenetrisulfonic acid), 8,8'-(carbonylbis(imino-4,1-phenylenecarbonylimino-4,1-phenylenecarbonylimino)bis(1,3,5-napththalenetrisulfonic acid), pyridoxal-5'-phosphate-6-(2'-naphthylazo-6-nitro-4', 8'-disulphonate), Suramin, and 2',3'-O-(2,4,6-trinitrophenyl) adenosine triphosphate.

Useful P2X2 receptor antagonists include Reactive blue 2 and Suramin.

Suitable P2X3 receptor antagonists are pyridoxal-5'-phosphate-6-azophenyl-2',5'-disulphonic acid, diinosine pentaphosphate, 8,8'-(carbonylbis(imino-3,1-phenylenecarbonylimino)bis(1,3,5-napththalenetrisulfonic acid), Suramin, and 2',3'-O-(2,4,6-trinitrophenyl)adenosine triphosphate.

Brilliant blue G can be utilized as a P2X4 receptor antagonist, while Suramin is a suitable P2X5 receptor antagonist.

In accordance with the present invention, the purine receptor antagonist is administered under conditions effective to treat spinal cord injury. Treatments may be prophylactic or may be used to treat existing conditions.

Effective amounts of the purine receptor antagonist will depend upon the mode of administration, frequency of administration, nature of the treatment, age and condition of the individual to be treated, and the type of pharmaceutical composition used to deliver the compound into a living system. Effective levels of purine receptor antagonists may range from 50 nM to 5 µM (given to experimental animals as 20-30 mg/kg twice daily for ten days), depending upon the compound, system, experimental and clinical endpoints, and toxicity thresholds. While individual doses vary, optimal ranges of effective amounts may be determined by one of ordinary skill in the art. For purine receptor antagonists that are involved in clinical trials for other indications, the safe and effective dosages identified in such trials can be considered when selecting dosages for treatments according to the present invention.

The purine receptor antagonists used according to the methods of the present invention can be administered alone or as a pharmaceutical composition, which includes the compound(s) and a pharmaceutically-acceptable carrier. The purine receptor antagonists are typically provided as a pharmaceutical composition. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of active compound(s), together with the carrier.

The purine receptor antagonist, when combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, such as, that of the nose, throat, and bronchial tubes (i.e., inhalation).

For most therapeutic purposes, the purine receptor antagonists can be administered orally as a solid or as a solution or suspension in liquid form, via injection as a solution or suspension in liquid form, or via inhalation of a nebulized solution or suspension. The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

For injectable dosages, solutions or suspensions of these materials can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose, and related sugar solution, and glycols, such as propylene glycol or polyethylene glycol, are preferred liquid carriers, particularly for injectable solutions.

For use as aerosols, the compound in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

For transdermal routes, the compound is present in a carrier which forms a composition in the form of a cream, lotion, solution, and/or emulsion. The composition can be included in a transdermal patch of the matrix or reservoir type as are conventional in the art for this purpose.

It is also contemplated that administration of the purine receptor antagonist can be carried out in combination with other suitable therapeutic treatments which are useful for treating spinal cord injury.

Another aspect of the present invention is directed to a method of treating a subject with spinal cord ischemia resulting from stroke or vascular insult, interruption, or mechanical injury. This method involves administering a purine receptor antagonist to the subject under conditions effective to treat spinal cord spinal cord ischemia resulting from stroke or vascular insult, interruption, or mechanical injury. The purine receptor antagonist inhibits P2X purine receptor activation. This aspect of the present invention is carried out in substantially the same manner as described above. Here, the mechanical injury is due to extradural cord compression, spinal cord trauma, or spinal cord surgery (e.g., aneurysmal repair or tumor resection).

A further aspect of the present invention relates to a method of treating a subject with ischemic or traumatic insults of brain tissue in regions expressing P2X receptors. This method involves administering a purine receptor antagonist to the subject under conditions effective to treat ischemic or traumatic insults of brain tissue in regions expressing P2X receptors. The purine receptor antagonist inhibits P2X purine receptor activation. This aspect of the present invention is carried out in substantially the same manner as described above.

Another aspect of the present invention relates to a method of inhibiting ATP-triggered brain or spinal cord cell death. This method is carried out by contacting brain or spinal cord cells with a purine receptor antagonist under conditions effective to inhibit ATP-triggered brain or spinal cord cell death. Causes of such brain cell death include vascular insufficiency, stroke, and traumatic brain injury. This method can be used with brain or spinal cord cells which are neural cells (e.g., neurons, oligodendrocytes, or astrocytes) as well as with endothelial cells. Preferably, all of these cell types are from humans. In this case, the purine receptor antagonist inhibits P2X purine receptor activation.

EXAMPLES

Example 1

Traumatic Model and Agonist Injections

Adult female Spague-Dawley rats (220-250 g) were anesthetized with pentobarbital (50 mg/kg i.p.). When unresponsive, a double level laminectomy was performed at the T11 and T12 vertebrae. Dura was left intact, and injury was produced by the NYU weight-drop impact by dropping a 5 g rod at an experimental height of 10 mm (Basso et al., "A Sensitive and Reliable Locomotor Rating Scale for Open Field Testing in Rats," *J Neurotrauma* 12:1-21 (1995), which is hereby incorporated by reference in its entirety). The tip of the rod was reduced to 1 mm to avoid direct traumatic injury of the dorsal venous complex. ATP and agonists (10 mM, 2 μl) were stereotaxically injected into T12 just lateral to the dorsal horn. All agents were purchased from Sigma.

Example 2

Bioluminescence Imaging of ATP

ATP release from the exposed spinal cord was imaged by chemiluminescence in real time as described in (Arcuino et al., "Intercellular Calcium Signaling Mediated by Point-Source Burst Release of ATP," *Proc Natl Acad Sci USA* 99:9840-9845 (2002), which is hereby incorporated by reference in its entirety). Luciferase (0.132 mg/ml) and luciferin (0.332 mg/ml) are added an artificial CSF solution containing (Nedergaard et al., "Characterization of cortical Depolarization Evoked in Focal Cerebral Ischemia," *J Cereb Blood Flow Metab* 13:568-574 (1993), which is hereby incorporated by reference in its entirety). Dura was kept intact, and the enzyme mixture delivered by a silastic tube inserted under dura at a rate of apprx. 1 ml/hr (Minipump RT-202, VWR). Light production from the luciferin-luciferase reaction was imaged by a liquid nitrogen-cooled CCD camera (VersArray 1300B, Princeton Instruments) using a 50 mm camera lens (Olympus), 4×4 binning, and 30 s integration/frame (Arcuino et al., "Intercellular Calcium Signaling Mediated by Point-Source Burst Release of ATP," *Proc Natl Acad Sci USA* 99:9840-9845 (2002), which is hereby incorporated by reference in its entirety)).

Example 3

Functional Outcome Analysis

The Basso, Beattie, and Bresnahan (BBB) 21-point open field locomotor rating scale was utilized for evaluation of hindlimb movements (Basso et al., "A Sensitive and Reliable Locomotor Rating Scale for Open Field Testing in Rats," *J Neurotrauma* 12:1-21 (1995), which is hereby incorporated by reference in its entirety)). The animals were evaluated daily for 2 weeks after injury and later on a biweekly basis.

Example 4

Tissue Preparation

Transcardiac perfusion are carried out in anesthetized rats 6 weeks after spinal cord injury by 4% paraformaldehyde in PBS (Takano et al., "Glutamate release Promotes Growth of Malignant Glioma," *Nat Med* 7:1010-1015 (2001), which is hereby incorporated by reference in its entirety)). The rats were anesthetized with ketamine (60 mg/kg) and xylazine (10 mg/kg). After 12 hours post-fixation, the spinal cord is cryoprotected in 30% sucrose and cut in serial 20 μm para-saggital sections. Myelin was visualized with Luxol fast blue (Basso et al., "A Sensitive and Reliable Locomotor Rating Scale for Open Field Testing in Rats," *J Neurotrauma* 12:1-21 (1995) and Nedergaard et al., "Characterization of Cortical Depolarization Evoked in Focal Cerebral Ischemia," *J Cereb Blood Flow Metab* 13:568-574 (1993), which are hereby incorporated by reference in their entirety)). Immunohistochemistry and TUNEL staining were performed as described in (Lin et al., "Gap-Junction-Mediated Propagation and Amplification of Cell Injury," *Nat Neurosci* 1:494-500 (1998); Lin et al., "Connexin Mediates Gap Junction-Independent Resistance to Cellular Injury," *J Neurosci* 23:430-441 (2003); and Takano et al., "Glutamate Release Promotes Growth of Malignant Glioma," *Nat Med* 7:1010-1015 (2001), which are hereby incorporated by reference in their entirety)). Immunofluorescence was visualized using confocal microscopy (BioRad MRC1024) and images analyzed by Metamorph software (Universal Imaging Corp.).

Example 5

Electrophysiology

Spinal cord slices were prepared from 10 to 14 day-old Sprague Dawley rats anesthetized with ketamine and xylazine. Section of the lumbar spinal cord (T9-L4) was rapidly dissected out and immersed in a ice-cold solution containing (in mM): 240 sucrose, 2.5 KCl, 0.5 $CaCl_2$, 10 $MgCl_2$, 26 $NaHCO_3$, 1.25 $NaH_2PO_4$, 10 glucose, and saturated with 95% $O_2$/5%$CO_2$. After isolation, the lumbar cord was immobilized in low-melting point agarose and transverse slices (300-350 μm) cut using a vibratome (TPI, St. Louis, Mo.). After sectioning, slices were transferred to an oxygenated artificial cerebrospinal fluid (ACSF) that contained (in mM): 125 NaCl, 2.5 KCl, 2 $CaCl_2$, 1 $MgCl_2$, 26 $NaHCO_3$, 1.25 $NaH_2PO_4$, and 10 glucose and allowed to recover for at least 1 hr before recording. Individual neurons were identified with a ×40 objective under infrared differential interference contrast microscopy (IR-DIC, Olympus BX61WI). The neurons were current clamped at their resting membrane potentials, ranging from −53 to −70 mV. The pipette solution contained (in mM): 10 KCl, 130 $KCH_3SO_3$, 2 $MgCl_2$, Hepes 20, 5 sodium phosphocreatine, 4 Mg-ATP, 0.3 GTP. Membrane currents were filtered at 1-2 KHz, digitized at 5-10 KHz using Axopatch 700A amplifier, Clampex8 software and DigiData 1332A interface (Axon Instruments Inc., Union City, Calif.). Series resistance (<20 M Ohms) was carefully monitored throughout the experiments and experiments were terminated if the series resistance changed more than 15%. All experiments were performed at room temperature (21-23° C.).

Example 6

Multi-Photon Laser Scanning Imaging

Calcium imaging was carried out with a custom-built two-photon laser scanning microscope linked to a Ti:sapphire laser (Mai Tai, Spectra-Physics, Mountain View, Calif.) using Fluoview software (Olympus, Melville, N.Y.) and a 60× objective (0.9 NA, IR, Olympus). Motor neurons were patched in whole-cell configuration with pipettes containing Alexa Fluor-594 (50 μM) and fluo-4 (100 μM) for a minimum of 20 min before imaging. Both fluorescence indicators were excited at 810 nm and the emission signal separated by emission filters.

Example 7

Imaging ATP Release Resulting From Spinal Cord Injury

A newly developed bioluminescence technique for imaging of live rats with acute spinal cord injury (Haydon, "GLIA: Listening and Talking to the Synapse," *Nat Rev Neurosci* 2:185-193 (2001), which is hereby incorporated by reference in its entirety)) was modified. By this approach, ATP release was monitored by light emissions resulting from ATP-triggered luciferase breakdown of luciferin. This process could be observed in real time, with a liquid nitrogen-cooled CCD camera (Arcuino et al., "Intercellular Calcium Signaling Mediated by Point-Source Burst Release of ATP," *Proc Natl Acad Sci USA* 99:9840-9845 (2002), which is hereby incorporated by reference in its entirety)) (FIG. 1). At baseline, the dorsal spinal cord exhibited low, but detectable levels of ATP release. An unexpected pattern of ATP release was observed in the traumatized spinal cord following a weight drop impact: The peri-traumatic zone was characterized by areas of sustained elevated ATP release. These zones of high ATP release were observed in all animals studied (n=24) and were in most animals restricted to 1 or 3 sharply demarcated areas (FIG. 1A). At 2 hrs after injury, the total area of high ATP release averaged 2.64±0.40 mm. A group of animals studied 6 hrs after impact, also displayed elevated ATP release, but the average total size was smaller, 1.46±0.25 $mm^2$ (n=6). At 24 hrs, no animals exhibited areas of increased ATP release (FIG. 1B). Cardiac arrest resulted in cessation of increased ATP release, ATP release from the traumatic lesion itself was depressed, likely a result of severe cellular damage and cessation of local ATP production. The traumatic lesion with low ATP release displayed a steady growth. Two hrs after injury the lesion averaged 0.68±0.06 $mm^2$, 0.88±0.04 $mm^2$ after 6 hrs, and 1.01 $mm^2$ after 24 hrs (FIG. 1C). These observations indicate that ATP release following acute spinal cord injury is characterized by depressed release from the traumatized tissue itself, but surrounded by zone of increased and sustained ATP release.

Example 8

Role of ATP Release in Delayed Spinal Cord Injury

To define the role of high ATP release in delayed injury, TUNEL staining was next used to analyze the extent of cell death in the peri-traumatic zone (Takano et al., "Glutamate Release Promotes Growth of Malignant Glioma," *Nat Med* 7:1010-1015 (2001, which is hereby incorporated by reference in its entirety)) (FIG. 2). Areas of high versus low ATP release were compared in equal distance to the traumatic lesion. Guided by bioluminescence imaging, $DiIC_{18}$ (2 μl, 10 μM) was locally injected to label the area of high ATP release as shown in FIG. 2A (n=10). The animals were perfusion-fixed 24 hrs later, and the $DiIC_{18}$ labeling was clearly recognizable on cryosections (FIG. 2B). Fast blue staining suggested that a considerable degree of myelin were lost in the areas of high ATP release, but less so on the opposite side of the lesion (FIG. 2C). Quantification of TUNEL positive cells showed that a significantly higher number of cells died in areas of high ATP release compared to tissue with low ATP release, despite their equal distance to the lesion (p=0.0004, student t-test) (FIG. 2D-F). Double staining with cell specific markers demonstrated that MAP-2 positive neurons, as well as O4 positive oligodendrocytes, but not GFAP positive astrocytes were TUNEL-positive in areas of high ATP release (FIG. 2E). Together, these observations indicate that cell injury is more severe in areas of sustained ATP release.

Example 9

Effect of Increased Extracellular ATP on Cell Death

It was then determined whether increased extracellular ATP in itself, in the non-injured spinal cord, was sufficient for induction of cell death. ATP or ATP analogs, all in a concentration of 10 mM (2 µl), were injected into the spinal cord just lateral to the dorsal horn. A large number of TUNEL-positive cells were present 24 hrs later in both gray and white matter (FIG. 2F). The highest extent of apoptosis was observed following injection of the non-degradable analog, ATPγS, but ATP itself also induced a significant extent of apoptosis (FIG. 2G). Surprisingly, the specific P2X7 receptor agonist BzATP induced apoptosis with a potency equivalent to ATP. This observation suggests that P2X7 receptor activation directly trigger cell death in spinal cord. In contrast, 2MeSATP and αβATP injections were not associated with significant injury, suggesting that other members of the P2X family played a minor role in ATP-induced apoptosis (FIG. 2G). These observations indicate that raising extracellular ATP concentration is sufficient for induction of cell death in the non-injured spinal cord. In this regard, P2X7 receptors are expressed by most immune cells and their activation leads to multiple downstream events, including cell permeabilization and apoptosis (Chow et al., "Purines and Their Roles in Apoptosis," *Neuropharmacology* 36:1149-1156 (1997) and Di Virgilio et al., "Cytolytic P2X Purinoceptors," Cell Death Differ 5:191-199 (1998), which are hereby incorporated by reference in their entirety)).

Example 10

Expression of P2X7 Receptors in Spinal Cord Neurons

A recent study has demonstrated widespread expression of P2X7 receptors throughout CNS (Deuchars et al., "Neuronal P2X7 Receptors Are Targeted to Presynaptic Terminals in the Central and Peripheral Nervous Systems," *J Neurosci* 21:7143-7152 (2001), which is hereby incorporated by reference in its entirety). It was confirmed that spinal cord neurons express numerous membrane localized P2X7 immunoreactive plaques (FIG. 3A). To evaluate the extent to which these receptors were functional, 2-photon laser scanning microscopy of freshly-prepared spinal cord slices (P14-2) was used to image neuronal cytosolic calcium. Spinal cord neurons were patched with a pipette solution containing fluo-4 (100 µM) and Alexa Fluor-594 (50 µM, to visualize fine processes). Bath application of either ATP or BzATP (both 100 µM) induced a sustained increase in cytosolic calcium concentration, detected by an increase in fluo-4 emission (FIG. 3B). The increase in cytosolic calcium remained high during 20 min agonist exposure and failed to normalize. Fifteen minutes after washout of ATP or BzATP, fluo-4 emission displayed a 200-300% increase relative to baseline (FIG. 3C). These observations indicated that prolonged exposure to ATP or BzATP is associated with an irreversible (and likely fatal) increase in neuronal cytosolic calcium concentration. To analyze the functional responses to ATP exposure, spinal cord neurons were patched and recorded in current clamp configuration. Exposure to ATP (100 µM) or BzATP (100 µM) consistently induced high frequency spiking with little tendency to inactivation (FIG. 4A). The increased spiking activity was attenuated by pretreatment with the P2X7 receptor antagonist OxATP (300 µM), but not by a combined treatment with CNQX/AP-5 suggesting that the action potentials were driven by the P2X7 linked channels, rather than by activation of NMDA/AMPA receptors. The affinity to either ATP and BzATP was low, with a kd 37.9± µM 23.8± µM, respectively. Combined these observations indicate that spinal cord neurons express functional P2X7 receptors, whose activation result in high frequency spiking and prolonged exposure is associated with irreversible increase in cytosolic $Ca^{2+}$.

Example 11

Protection Against Cell Death Following Spinal Cord Injury

It was next determined whether OxATP protected against cell death in the area of high ATP release following spinal cord injury. OxATP (1 mM, 2 µl) was injected locally into the peri-traumatic zone immediately prior to impact. Ox-ATP treated animals sacrificed 24 hrs later displayed a highly significant reduction in number of TUNEL positive cells surrounding the lesion compared to matched vehicle controls (FIGS. 5A-B). The BBB open field locomotor rating scale was used to evaluate recovery of rats receiving OxATP versus vehicle treated control. Remarkably, animals pretreated with OxATP exhibited a significant improved recovery compared with vehicle-treated controls (n=14 in both groups) (FIG. 5C). The animals treated with OxATP scored 2-4 points higher during the first week of recovery, and exhibited a more rapid recovery, resulting in 6 to 8 points difference during the remaining part of the observation period. Combined, these observations indicate that OxATP effectively reduced tissue damage and improved functional recovery following spinal cord injury.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating secondary injury associated with acute spinal cord injury in a subject, said method comprising:
   administering a P2X7 purine receptor antagonist to the subject under conditions effective to inhibit the P2X7 purine receptor in regions peritraumatic to the spinal cord injury, whereby secondary injury associated with acute spinal cord injury in the subject is treated.

2. The method according to claim 1, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

3. The method according to claim 1, wherein the purine receptor antagonist is administered with a pharmaceutically-acceptable carrier.

4. The method according to claim 1, wherein the subject is a human.

5. The method according to claim 1, wherein the P2X7 purine receptor antagonist is selected from the group consisting of 1-[N,O-bis(5-Isoquinolinesulfonyl)-N-methyl-L-tyrosyl]-4-phenylpiperazine, hexamethylene amiloride, oxidized ATP, and brilliant blue G.

6. A method of treating a subject with spinal cord ischemia resulting from stroke or vascular insult, interruption, or mechanical injury in regions peritraumatic to the stroke or vascular insult, interruption, or mechanical injury, said method comprising:

administering a P2X7 purine receptor antagonist to the subject under conditions effective to treat spinal cord ischemia resulting from stroke or vascular insult, interruption, or mechanical injury in regions peritraumatic to the stroke or vascular insult, interruption, or mechanical injury.

7. The method according to claim 6, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

8. The method according to claim 6, wherein the purine receptor antagonist is administered with a pharmaceutically-acceptable carrier.

9. The method according to claim 6, wherein the subject is a human.

10. The method according to claim 6, wherein the P2X7 purine receptor antagonist is selected from the group consisting of 1-[N,O-bis(5-Isoquinolinesulfonyl)-N-methyl-L-tyrosyl]-4-phenylpiperazine, hexamethylene amiloride, oxidized ATP, and brilliant blue G.

11. The method according to claim 6, wherein the mechanical injury is due to extradural cord compression, spinal cord trauma, or spinal cord surgery.

12. A method of inhibiting ATP-triggered brain or spinal cord cell death of cells peritraumatic to a direct injury, said method comprising:

contacting brain or spinal cord cells with a P2X7 purine receptor antagonist under conditions effective to inhibit ATP-triggered brain or spinal cord cell death of cells peritraumatic to the direct injury.

13. The method according to claim 12, wherein the brain or spinal cord cells are neural cells.

14. The method according to claim 13, wherein the neural cells are astrocytes.

15. The method according to claim 13, wherein the neural cells are neurons.

16. The method according to claim 13, wherein the neural cells are oligodendrocytes.

17. The method according to claim 12, wherein the brain or spinal cord cells are endothelial cells.

18. The method according to claim 12, wherein the method inhibits ATP-triggered brain cell death.

19. The method according to claim 18, wherein the brain cell death results from vascular insufficiency.

20. The method according to claim 18, wherein the brain cell death results from stroke.

21. The method according to claim 18, wherein the brain cell death results from traumatic brain injury.

22. The method according to claim 12, wherein the method inhibits ATP-triggered spinal cord cell death.

23. The method according to claim 12, wherein the brain or spinal cord cells are human brain or spinal cord cells.

24. The method according to claim 12, wherein the P2X7 purine receptor antagonist is selected from the group consisting of 1-[N,O-bis(5-Isoquinolinesulfonyl)-N-methyl-L-tyrosyl]-4-phenylpiperazine, hexamethylene amiloride, oxidized ATP, and brilliant blue G.

25. The method of claim 1 further comprising:

selecting a subject with acute spinal cord injury prior to said administering, wherein the P2X7 purine receptor antagonist is administered to the selected subject.

26. The method of claim 6 further comprising:

selecting a subject with spinal cord ischemia resulting from stroke or vascular insult, interruption, or mechanical injury prior to said administering, wherein the P2X7 purine receptor antagonist is administered to the selected subject.

* * * * *

UNITED STATES PATENT AND TRADEMARK OFFICE
CERTIFICATE OF CORRECTION

PATENT NO. : 7,923,448 B2
APPLICATION NO. : 10/979526
DATED : April 12, 2011
INVENTOR(S) : Maiken Nedergaard et al.

It is certified that error appears in the above-identified patent and that said Letters Patent is hereby corrected as shown below:

Column 1, line 8, "grant 30007" should read --grant NS030007--.

Signed and Sealed this
Eleventh Day of October, 2011

David J. Kappos
*Director of the United States Patent and Trademark Office*